United States Patent [19]

Schmidt et al.

[11] 4,452,737
[45] Jun. 5, 1984

[54] SURFACE-ACTIVE AZO COMPOUNDS

[75] Inventors: Adolf Schmidt, Cologne; Ernst Roos, Odenthal, both of Fed. Rep. of Germany

[73] Assignee: Bayer Aktiengesellschaft, Leverkusen, Fed. Rep. of Germany

[21] Appl. No.: 373,962

[22] Filed: May 3, 1982

[30] Foreign Application Priority Data

May 9, 1981 [DE] Fed. Rep. of Germany ....... 3118372

[51] Int. Cl.³ .................. B01F 17/00; B01F 17/26; C07C 107/02; C08F 4/04
[52] U.S. Cl. ............................ 260/192; 252/351; 252/357; 252/358; 260/193; 526/218.1; 526/219
[58] Field of Search ............................. 260/192, 193

[56] References Cited

U.S. PATENT DOCUMENTS 2,599,299 6/1952 Upson .................... 260/192
2,794,834 6/1957 Randall et al. ................. 260/556
3,161,630 12/1964 Phelisse et al. ................ 260/192

*Primary Examiner*—Floyd D. Higel
*Attorney, Agent, or Firm*—Connolly and Hutz

[57] ABSTRACT

The invention relates to surface-active azo compounds obtainable by reacting azo compounds corresponding to the following general formula (I):

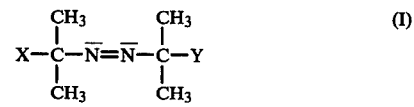

in which X and Y are the same or different and represent

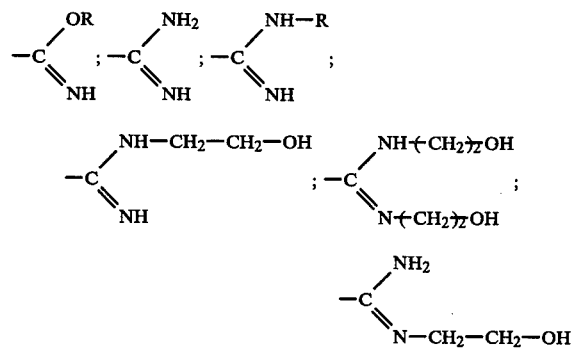

and
R represents $C_1$–$C_4$-alkyl, with at least one $C_{10}$–$C_{18}$-paraffin disulphonic acid dihalide in aqueous medium or a solvent or solvent mixture which is inert to the reactants under the process conditions and in which the reactants are at least partly soluble, at temperatures in the range of from 0° to +° C. and in the presence of a base in a quantity substantially equivalent to the hydrolysable halogen, the reaction being accompanied by the elimination of hydrogen halide. The new azo compounds give low electrolyte, low-foam dispersions in emulsion and dispersion polymersation.

3 Claims, No Drawings

SURFACE-ACTIVE AZO COMPOUNDS

This invention relates to water-soluble, surface-active substances containing azo and paraffin sulphonate groups which may be used as emulsifying initiators in the production of low-electrolyte dispersions having a minimal tendency towards foaming based on olefinically unsaturated monomers.

It is known that azodiisobutyric acid amidine and derivatives thereof, for example N-alkylation and N-alkoxylation products in the form of the salts or free bases, may be used as water-soluble initiators in the emulsion polymerisation of olefinically unsaturated monomers (cf. U.S. Pat. Nos. 2,599,300 and 2,810,702 and DE-OS No. 2,841,045).

It is also known that alkyl sulphonates may be used as anion-active emulsifiers in the emulsion polymersiation of olefinically unsaturated monomers [cf. Methoden der Organischen Chemie, Houben-Weyl, Vol 14/1 (1961) pages 196 to 198].

However, the dispersions prepared in the presence of the above-mentioned azo initiators and emulsifiers have a tendency to foam. Accordingly, an object of the present invention is to provide an initiator/emulsifier system with which it is possible to produce dispersions having a minimal tendency towards foaming. At the same time. the dispersions are intended to have as low an electrolyte content as possible.

According to the invention, this object is achieved by the provision of new surface-active azo compounds containing incorporated paraffin sulphonate groups which show both emulsifying and activating properties. These new substances act initially as emulsifiers and decompose during the polymerisation reaction, the catalyst fragments containing the paraffin sulphonate groups being incorporated into the polymer and protecting the latex particles against coagulation.

Accordingly, the present invention provides surface-active compounds obtainable by reacting azo compounds corresponding to the following general formula (I):

$$X-\underset{\underset{CH_3}{|}}{\overset{\overset{CH_3}{|}}{C}}-\overline{N}=\overline{N}-\underset{\underset{CH_3}{|}}{\overset{\overset{CH_3}{|}}{C}}-Y \quad (I)$$

in which X and Y may be the same or different and each represents one of the following:

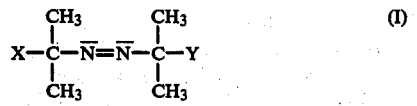

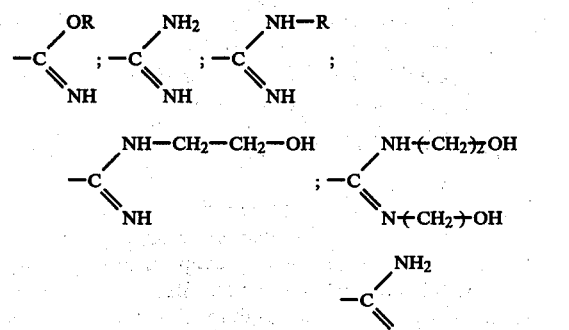

and

R represents $C_1$–$C_4$-alkyl, with at least one $C_{10}$–$C_{18}$-paraffin disulphonic acid dihalide in aqueous medium or in a solvent or a solvent mixture which is inert to the reactants under the process conditions and in which the reactants are at least partly soluble, at temperatures in the range of from 0° to 30° C. and in the presence of a base in a quantity substantially equivalent to the hydrolysable halogen, the reaction being accompanied by the elimination of hydrogen halide.

Preferred radicals X and Y are

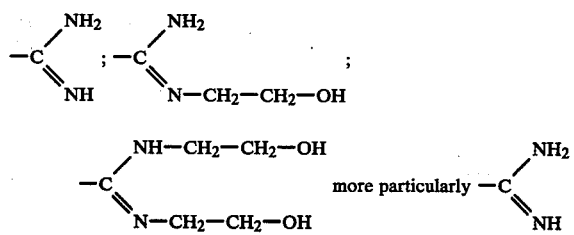

The azo compounds corresponding to general formula (I) are known, as are the $C_{10}$–$C_{18}$-paraffin disulphonic acid dihalides used in accordance with the invention. $C_{10}$–$C_{18}$-paraffin disulphonic acid dichlorides are preferred, $C_{14}$–$C_{16}$-paraffin disulphonic acid dichlorides being particularly preferred. It is preferred to use mixtures of the paraffin disulphonic acid dichlorides (for production, see F. Asinger, Die petrolchemische Industrie, Part I, pages 731 to 738, Akademie-Verlag Berlin 1971). The paraffin disulphonic acid dichlorides may still contain small quantities of halogen (up to about 5% by weight) in the paraffin chain from their production. The above-mentioned numbers of carbon atoms in the paraffin disulphonic acid dihalides are average values.

The reaction of aromatic monosulphonic acid chlorides with monofunctional imino ethers or monofunctional amidines is known per se.

In the reaction of sulphonyl chlorides with imino ether bases, sulphonyl amides are formed in addition to the sulphonyl iminoethers. The reaction of sulphonyl chlorides with amidines is accompanied by the formation of tautomeric sulphonyl amidines differing in their stability which are capable of forming different hydrolysis products in the presence of water (cf. H. J. Barber, J. Chem. Soc. 1943, 101–104).

To produce the surface-active azo compounds, it is preferred to use from 1 to 2 moles and, more particularly, approximately 2 moles of the paraffin disulphonic acid dihalides per mole of azo compound corresponding to general formula (I) or its salts.

The reaction is carried out at temperatures below the decomposition temperature of the azo compounds, preferably at temperatures in the range of from 0° to 30° C. and, more particularly, at temperatures in the range of from 5° to 20° C.

Alkali metal or alkaline-earth metal hydroxides or ammonia in the form of their aqueous solutions, preferably alkali metal hydroxides, such as sodium or potassium hydroxide, are used as the bases in a quantity substantially equivalent to the halogen (hydrolysable at 0° to 30° C.) of the disulphonic acid dihalide groups. Where the azo compounds corresponding to general formula (I) are used in the form of their salts, the quantity of bases is increased to such an extent that the azo compounds corresponding to formula (I) are present as bases. The halogen optionally present in the paraffin chain of the paraffin disulphonic acid dihalides is not hydrolysed to any significant extent by the bases under the prevailing reaction conditions.

The preferred reaction medium is water, although it is also possible to use solvents, such as pyridine, tetrahydrofuran, dimethyl formamide, or ketones, such as acetone, or mixtures of these solvents as the reaction medium.

The reaction of the azo compounds corresponding to general formula (I) or their salts with the paraffin disulphonic acid dihalides may advantageously be carried out by initially introducing the azo compound in solution in the reaction medium, preferably water, and adding the paraffin disulphonic acid dihalide and the base separately, but at the same time, at a substantially constant temperature in the range of from 0° to 30° C. The pH-value of the reaction mixture should be kept in the range of from 7 to 10 during the reaction. The reaction is exothermic and is kept at the temperature selected by suitable cooling measures. On completion of the reaction, the reaction medium is neutral to mildly alkaline (pH: 7–8.5).

The reaction mixture may be worked up by careful evaporation to dryness. Methanol or ethanol is then added to the residue, the azo compounds containing sulphonate groups passing into solution. In this form, they may readily be separated off from the salts. Removal of the alcohol by evaporation leaves the salt-free surface-active azo compounds containing sulphonate groups.

Another possible method of working up the aqueous reaction mixture is to extract it with suitable water-immiscible solvents, such as low-boiling ethers.

The surface-active azo compounds obtained in accordance with the invention are water-soluble, waxlike to syrupy substances which have average molecular weights $\overline{M}_n$ (number average) of from 0.8 to $3.0 \times 10^3$, as determined by membrane osmometry taking into account the STAVERMANN coefficient. As confirmed by thin layer chromatography, IR-spectra and azo group determination, they contain azo groups and sulphonate groups, but are substantially free from paraffin disulphonates, i.e. hydrolysis products of the paraffin disulphonic acid dihalides. It is not possible to give an exact structural formula for the emulsifying azo initiators because they are mixtures of substances. The azo compounds according to the invention have good emulsifying properties.

Accordingly, the present invention also relates to their use in the emulsion and dispersion polymerisation of one or more olefinically unsaturated monomers. The surface-active azo compounds are used in salt form, preferably in the form of alkali metal salts, in quantities of from 1.5 to 5% by weight an preferably in quantities of from 2 to 3% by weight, based on monomer.

The surface-active azo compounds according to the invention may be handled in the same way as standard emulsifiers during the polymerisation reaction. In other words, they may either be introduced all at once at the beginning or, alternatively, may be partly introduced at the beginning of and partly during the emulsion polymerisation reaction (run-in process).

The polymerisation reaction is preferably carried out at temperatures in the range of from 35° C. to 90° C., depending on the decomposition kinetics of the azo emulsifiers. The most preferred temperature range is from 45° C. to 75° C.

Suitable polymerisable monomers are any of the olefinically unsaturated monomers which normally polymerise with azo diisobutyric acid nitrile, for example styrene, α-methyl styrene, butadiene, acrylic acid esters containing from 1 to 8 carbon atoms in the alcohol component, methacrylic acid esters containing from 1 to 8 carbon atoms in the alcohol component, acrylonitrile, methacrylonitrile, vinyl chloride, vinyl acetate, ethylene, isoprene, chloroprene etc.

In addition to the above-mentioned monomers, water-soluble compounds, such as methacrylic acid, acrylic acid, maleic acid semi-ester, itaconic acid and itaconic acid semi-ester, acrylamide, methacrylamide, etc., may be additionally incorporated in the polymer in a smaller quantity. In addition, it is possible to use comonomers containing functional groups, for example OH-groups or epoxy groups, such as β-hydroxyethyl (meth)-acrylate, β-hydroxy propyl (meth)acrylate, glycidyl (meth)acrylate and N-methylol or N-methylol alkyl ethers of (meth)acrylic acid amide.

It is, of course, possible in principle to use the emulsifying azo compounds according to the invention in admixture with standard anionic or nonionic emulsifiers.

The advantageous and surprising properties of the azo compounds according to the invention will become apparent from the following Examples and Comparison Examples. The parts and percentages quoted in the Examples and Comparison Examples are based on weight, unless otherwise indicated.

EXAMPLE 1

(Azo emulsifier A according to the invention)

90 g of azo diisobutyric acid amidine (0.45 mole) corresponding to the following formula

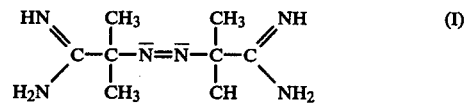

are dissolved with vigorous stirring in 400 ml of ice-cold deionised water. Immediately after the amidine has dissolved, 372 g of a mixture of sulphochlorinated paraffins having a sulpho chlorine content of approximately 17%, a total chlorine content of approximately 20.5% and an average C-number of 15 and, at the same time, 217.8 g of 50% sodium hydroxide solution are added dropwise over a period of 30 minutes while cooling with ice (external cooling: internal temperature approximately +10° C.) to the solution of the azo diisobutyric acid amidine at a pH-value of from 7 to 10. After the paraffin sulphochloride mixture and the sodium hydroxide have been added, the reaction mixture is stirred at 15° to 20° C. until it has a pH-value of approximately 8.

The water present in the reaction mixture may be removed in vacuo (approximately 1 mbar) therefrom without foaming using a rotary evaporator. The pasty residue is stirred with methanol, the azo emulsifiers passing into solution and sodium chloride remaining behind. After the sodium chloride and a small fraction insoluble in methanol (approximxately 125 g of dried filter residue, Cl-content approximately 50%) have been filtered off under suction, the methanolic filtrate is concentrated in vacuo at approximately 30° C. in a rotary evaporator, leaving behind a yellow, wax-like substance mixture. Yield: 440 g (azo emulsifier A).

It was shown by thin-layer chromatography (chloroform/methanol mixture 65:35) that the azo diisobutyric acid amide rapidly formed from azodiisobutyric acid amidine in the presence of water and the disulphonates formed by hydrolysis of the sulphochlorinated paraffins are only present in traces in the azo emulsifier mixture.

The IR-spectrum of the anhydrous, solid azo emulsifier A, as measured using a KBr-pellet, shows the $\nu(S=O)$-bands characteristic of sulphonate groups at 1190 and 1050 cm$^{-1}$. In the carbonyl region, absorption bands appear at 1680 (shoulder) and 1640 and also at 1550 cm$^{-1}$, indicating the linking structural elements

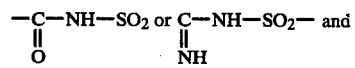

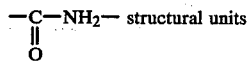 structural units as non-linking elements.

A value of less than $2.5 \times 10^3$ was determined by membrane osmometry as the average molecular weight (number average). According to determination by gel chromatography, the average molecular weight is approximately $10^3$.

The azo emulsifier A may also be similarly produced from azodiisobutyric acid amidine dihydrochloride. In this case, a correspondingly larger quantity of sodium hydroxide is used for binding the hydrochloric acid (2 moles of NaOH more than indicated above per mole of azo compound).

EXAMPLE 2

(Polymerisation tests using azo emulsifier A (Table 1a, b, c) and Comparison Tests c, d and e)

Series polymerisation tests were carried out in the absence of air in 500 ml capacity corked glass bottles fitted with an additional crown cork closure [cf. Houben-Weyl, Methoden der Organischen Chemie, Vol. 14/1, page 147 (1961)]. The glass bottles were put in fine steel baskets for protection against shattering and rotated at a speed of 25 revolutions per minute. The temperature of the water bath was kept constant. The corks of the bottles were pierced by means of a steel cannula before their removal from the steel baskets in order to release any excess pressure which may have built up.

In Table I, the mode of action of azo emulsifier A produced in accordance with Example 1 is compared with that of a mixture consisting of azodiisobutyric acid amidine as initiator and a quantity corresponding to the azo emulsifier of a standard commercial, secondary alkane monosulphonate based on unbranched paraffins containing an average of 15 carbon atoms.

Where the azo emulsifier A is used, the coagulate content of the dispersions is only slightly higher than in the comparison test. However, the solids content where azo emulsifier A is used is distinctly higher. The dispersions produced in accordance with the invention are remarkable in particular for their lower electrical conductivity and their lower tendency towards foaming. The surface tension, which is inversely proportional to the number of drops as measured with a stalagmometer (liquid volume 1 ml)—the drop count is a measure of surface tension and is defined as the number of drops into which 1 cc of solution or latex is dispersed at room temperature (22° C.)—is of course still low even where relatively large quantities of azo emulsifier are used, but decreases distinctly where relatively large quantities of conventional surfactants are used (cf. test c with f in Table I, line 12 "Drop count latex").

There is no significant difference between the size of the latex particles (cf last line of Table I) when corresponding quantities of azo emulsifier or alkali metal alkane monosulphonate are used. A 10% aqueous solution of the azo emulsifier A used has an electrical conductivity of approximately 14 mS whilst a corresponding 10% solution of the alkali metal alkane monosulphonate shows a conductivity of approximately 14.4 mS in water. Accordingly, if the emulsifier solutions used differ only slightly in their electrical conductivity, there is a distinct difference in electrical conductivity between the polymer dispersions produced with the various emulsifier systems.

The instrument used to measure conductivity produced the following conductivity readings for potassium chloride solutions at room temperature:

| | C (mol/l)KCl | Conductivity (mS) |
|---|---|---|
| 0.0745 g KCl/l | $10^{-3}$ | 0.12 |
| 0.746 g KCl/l | $10^{-2}$ | 1.3 |
| 7.456 g KCl/l | $10^{-1}$ | 11.2 |

TABLE I

| | Invention | | | Comparison | | |
|---|---|---|---|---|---|---|
| | a | b | c | d | e | f |
| Deionised water (g) | 163.6 | 152.8 | 109.6 | 159.1 | 148.3 | 105.1 |
| Styrene, distilled (g) | 100 | 100 | 100 | 100 | 100 | 100 |
| Azo emulsifier A, 10% in water (g) | 36.0 | 48.0 | 96.0 | — | — | — |
| Alkali metal alkane monosulphonate containing approximately 15 carbon atoms, 10% in water (Na—salts) in g | — | — | — | 36.0 | 48.0 | 96.0 |
| Azodiisobutyric acid amidine, 10% in water, in g | — | — | — | 5.0 | 5.0 | 5.0 |
| Polymerisation time (h) | 7 | 7 | 7 | 7 | 7 | 7 |
| Polymerisation temperature (°C.) | 60 | 60 | 60 | 60 | 60 | 60 |
| Characterisation of the disperions Coagulate content (g) | 0.8 | 0.8 | 0.9 | 0.6 | 0.5 | 0.2 |
| Solids content (%) | 32.9 | 34.0 | 34.8 | 31.9 | 33.8 | 30.8 |
| Electrical conductivity (mS) | 1.6 | 2.1 | 3.6 | 2.5 | 2.9 | 4.6 |
| Foam collapse in [sec.] after vigorous shaking for 30 seconds | 100 | 130 | 180 | >300 | >300 | >300 |
| Drop count latex (stalagmometer) | 32 | 33 | 31 | 30 | 30 | 60 |
| Drop count water (stalagmometer) | 30 | 30 | 30 | 30 | 30 | 30 |
| Latex particle diameter (nm) according to laser correlation spectroscopy (LCS) | 113 | 107 | 94 | 108 | 107 | 95 |

EXAMPLE 3

(According to the invention a-f and Comparisons g-r)

Following the same procedure as described in Example 2, an n-butyl acrylate/styrene monomer mixture is copolymerised in emulsion in accordance with the invention in the presence of azo emulsifier A (Table II, tests a-f).

The Table II, a-f series, is compared with corresponding tests, in which a sodium alkane monosulphonate mixture is used as emulsifier and azodiisobutyric acid amidine as the initiator and in which the ratio by weight of emulsifier to initiator, i.e. the ratio by weight of sec. alkane monosulphonate to azodiisobutyric acid amidine, is kept constant (Table II, tests g-l).

In tests m to r in Table II, the secondary alkane monosulphonate was replaced by a sodium-chloride-free alkane disulphonate which had been obtained by hydrolysing the mixture of sulphochlorinated paraffins mentioned in Example 1 with aqueous sodium hydroxide.

The comparison tests show that the dispersions produced in accordance with the invention have a lower tendency towards foaming and lower electrical conductivity.

In regard to latex particle size, tests a to f in Table II largely correspond to tests g to l in Table II. By contrast, the dispersions prepared in the presence of the alkali metal disulphonate emulsifier are characterised by much larger particles. This observation is consistent with the fact that the disulphonates formed by hydrolysis of the sulphochlorinated paraffins are only present in traces of azo emulsifier A (cf. Example 1).

TABLE II

| | Invention | | | | | |
|---|---|---|---|---|---|---|
| | a | b | c | d | e | f |
| Deionised water (parts) | 191.7 | 185.2 | 174.4 | 163.6 | 152.8 | 109.6 |
| n-Butyl acrylate (parts) | 57.3 | 57.3 | 57.3 | 57.3 | 57.3 | 57.3 |
| Styrene (parts) | 42.7 | 42.7 | 42.7 | 42.7 | 42.7 | 42.7 |
| Azo emulsifier A, 10% in water (parts) | 4.8 | 12.0 | 24.0 | 36.0 | 48.0 | 96.0 |
| Alkane monosulphonate (Na—salts) containing approximately 15 carbon atoms, 10% in water, (parts) | — | — | — | — | — | — |
| Alkane disulphonate (Na—salts) containing approximately 15 carbon atoms, 10% in water, (parts) | — | — | — | — | — | — |
| Azodiisobutyric acid amidine, 10% in water (parts) | — | — | — | — | — | — |
| Polymerisation temperature (°C.) | 60→ | → | → | → | → | → |
| Polymerisation time (h) | 7→ | → | → | → | → | → |
| Precipitate (parts) | 3.1 | 2.0 | 1.0 | 0.7 | 0.6 | 0.6 |
| Solids content latex (% by weight) | 28.3 | 31.0 | 33.1 | 34.1 | 34.6 | 35.2 |
| Foam collapse in [sec.] after vigorous shaking for 30 seconds | 5 | 10 | 15 | 25 | 60 | 250 |
| Electrical conductivity (mS) | 0.38 | 0.88 | 2.21 | 2.33 | 2.80 | 4.80 |
| Particle size (nm) as determined by LCS | 167 | 132 | 115 | 100 | 97 | 79 |
| Drop count water | 24 | 24 | 24 | 24 | 24 | 24 |
| Drop count latex | 32 | 34 | 32 | 32 | 32 | 36 |

| | Comparison | | | | | |
|---|---|---|---|---|---|---|
| | g | h | i | j | k | l |
| Deionised Water (parts) | 191.7 | 185.2 | 174.4 | 163.6 | 152.8 | 109.6 |
| n-Butyl acrylate (parts) | 57.3 | 57.3 | 57.3 | 57.3 | 57.3 | 57.3 |
| Styrene (parts) | 42.7 | 42.7 | 42.7 | 42.7 | 42.7 | 42.7 |
| Azo emulsifier A, 10% in water (parts) | — | — | — | — | — | — |
| Alkane monosulphonate (Na—salts) containing approximately 15 carbon atoms, 10% in water (parts) | 3.8 | 9.5 | 19.0 | 28.5 | 38.0 | 76.0 |
| Alkane disulphonate (Na—salts) containing approximately 15 carbon atoms, 10% in water (parts) | — | — | — | — | — | — |
| Azodiisobutyric acid amidine, 10% in water (parts) | 1.0 | 2.0 | 5.0 | 7.5 | 10.0 | 20.0 |
| Polymerisation temperature (°C.) | 60→ | → | → | → | → | → |
| Polymerisation time (h) | 7→ | → | → | → | → | → |
| Precipitate (parts) | 3.4 | 2.2 | 0.7 | 0.5 | 0.25 | 0.1 |
| Solids content latex (% by weight) | 31.7 | 33.2 | 33.7 | 33.8 | 34.8 | 34.6 |
| Foam collapse in [sec.] after vigorous shaking for 30 seconds | 10 | 15 | 35 | <300 | <300 | <300 |
| Electrical conductivity (mS) | 0.66 | 1.45 | 2.52 | 3.50 | 4.50 | 7.80 |
| Particle size (nm) as determined by LCS | 166 | 115 | 100 | 94 | 90 | 79 |
| Drop count water | 24 | 24 | 24 | 24 | 24 | 24 |
| Drop count latex | 28 | 30 | 34 | 36 | 40 | 49 |

| | Comparison | | | | | |
|---|---|---|---|---|---|---|
| | m | n | o | p | q | r |
| Deionised water (parts) | 191.7 | 185.2 | 174.4 | 163.6 | 152.8 | 109.6 |
| n-Butyl acrylate (parts) | 57.3 | 57.3 | 57.3 | 57.3 | 57.3 | 57.3 |
| Styrene (parts) | 42.7 | 42.7 | 42.7 | 42.7 | 42.7 | 42.7 |
| Azo emulsifier A, 10% in water (parts) | — | — | — | — | — | — |
| Alkane monosulphonate (Na—salts) containing approximately 15 carbon atoms, 10% in water, (parts) | — | — | — | — | — | — |

TABLE II-continued

| | | | | | | |
|---|---|---|---|---|---|---|
| Alkane disulphonate (Na—salts) containing approximately 15 carbon atoms, 10% in water, (parts) | 3.8 | 9.5 | 19.0 | 28.5 | 38.0 | 76.0 |
| Azodiisobutyric acid amidine, 10% in water (parts) | 1.0 | 2.5 | 5.0 | 7.5 | 10.0 | 20.0 |
| Polymerisation temperature (°C.) | 60→ | → | → | → | → | → |
| Polymerisation time (h) | 7→ | → | → | → | → | → |
| Precipitate (parts) | 3.1 | 2.5 | 1.5 | 1.2 | 1.1 | 0.5 |
| Solids content latex (% by weight) | 27.6 | 30.1 | 31.3 | 34.5 | 31.2 | 31.4 |
| Foam collapse in [sec.] after vigorous shaking for 30 seconds | 30 | 30 | 70 | <300 | <300 | <300 |
| Electrical conductivity (mS) | 0.85 | 2.0 | 3.5 | 4.8 | 6.8 | 10.8 |
| Particle size (nm) as determined by LCS | 240 | 185 | 153 | 153 | 150 | 220 |
| Drop count water | 24 | 24 | 24 | 24 | 24 | 24 |
| Drop count latex | 32 | 33 | 34 | 33 | 36 | 42 |

EXAMPLE 4 (Comparison Examples)

The following compounds were used without the assistance of emulsifiers for the polymerisation of a mixture of n-butyl acrylate and styrene:

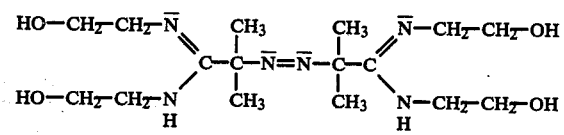

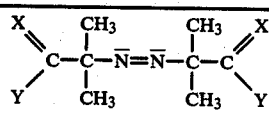

(a) X = NH;   Y = —NH$_2$
(b) X = NH;   Y = —NH$_3^+$Cl$^-$
(c) X = NH;   Y = —O—C$_2$H$_5$
(d) X = N—CH$_2$—CH$_2$—OH;   Y = —NH—CH$_2$—CH$_2$—OH
(e) X = N—CH$_2$—CH(OH)—CH$_3$;   Y = —NH—CH$_2$—CH(OH)—CH$_3$
(f) X = N—CH$_2$—CH(OH)—CH$_3$;   Y = —NH$_2$

In addition, the following compound

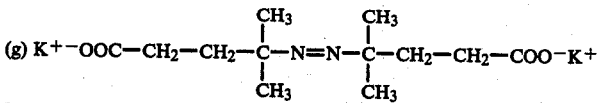

is tested as an "azo emulsifier."

The tests were carried out in the same way as tests a to f of Example 3, Table II, under the same conditions (60° C., 7 hours). Compounds a to g were used in the same quantities by weight. Evaluation of the tests (42 in all) showed that in not one case could a latex be obtained. Instead, a viscous paste having a high monomer content was formed in the case of compound (a), a coagulate in the case of compund (b), a viscous paste having a high monomer content in the case of compound (c) paste and coagulate in the case of compound (d), no polymer in the case of compound (e), no polymer or coagulate in the case of compound (f) and no polymer in the case of compound (g).

EXAMPLE 5

[Azo emulsifier B (according to the invention)]

50 g (0.134 mole) of azodiisobutyric acid-(N,N'-bis-hydroxyethyl)-amidine (M=374) and, at the same time, a solution of 32.1 g (0.8 mole) of NaOH in 100 g of distilled water are added while stirring and cooling with a mixture of ice and sodium chloride (external cooling: external temperature approximately −15° C.) to 109.2 g (0.27 mole) of a mixture of sulphochlorinated paraffins (average C-number 15, sulpho chlorine content 17%, corresponding to 2 sulphochlorine groups per C-15 alkane and, in addition, 3 to 4.5% of C-chain chlorine) at a pH-value in the range of from 7 to 10 at such a rate that the internal temperature does not rise above +30° C.

On completion of the reaction, the reaction mixture has a pH-value of 8 and is transparent and honeybrown in colour. The water is carefully removed in vacuo in a rotary evaporator, which may be done in the absence of any foaming.

The residue is stirred with ethanol (approximately 700 ml), sodium chloride accumulating in coarsely crystalline, readily filterable form (30 g) and the azo emulsifier passing into solution. Removal of the alcohol and drying of the residue (for 60 minutes at 30° C./approximately 0.5 mbar) leaves 125 g of a paste which is readily soluble in water, Part of this paste is carefully dried over phosphorus pentoxide in a drying gun (5 hours at 30°). Composition of the substance mixture as determined by elemental analysis:

% C: 47.5; % H: 8.3; % N: 7.1; % O: 19.4; % S: 10.5; % Cl: 3.2. Remainder $Na^{\oplus}$.

Since the product in question is a mixture, it is not possible to give an exact structural formula.

A value of less than $2.5 \times 10^3$ was determined by membrane osmometry as the average molecular weight (number average).

According to determination by gel chromatography the average molecular weight amounts to approximately $10^3$.

The dilute aqueous solution of azo emulsifier B foams, and, in a concentration of 10% by weight, has an electrical conductivity of 13.8 mS. A solution of 7.46 g of KCl in 1 liter of water (0.1 mole/liter) has a conductivity of 12 mS, as measured with the same instrument.

The drop count of 50 g of water is increased as follows by the addition of a 10% solution of azo emulsifier B:

| Addition of azo emulsifier B in ml, 10% solution | Drop count of 1 ml of aqueous solution after the addition of B to 50 g of water |
|---|---|
| 0 (pure water) | 25 |
| 0.2 | 27 |
| 0.4 | 32 |
| 0.6 | 38 |
| 0.8 | 43 |
| 1.0 | 47 |
| 1.2 | 49 |
| 1.4 | 50 |
| 1.6 | 52 |
| 1.8 | 54 |
| 2.2 | 54 |
| 2.8 | 56 |
| 3.6 | 57 |
| 5.2 | 58 |
| 8.0 | 58 |

Accordingly, azo emulsifier B shows typical surfactant properties.

EXAMPLE 6

Polymerisation tests with azo emulsifier B

The polymerisation tests summarised in Table III are carried out in the same way as in Example 2.

Accordingly, it is also possible using azo emulsifier B to produce finely divided, low-foam dispersions.

TABLE III

| Test | IIIa | IIIb | IIIc | IIId |
|---|---|---|---|---|
| Deionised water (parts) | 152.8 | 163.60 | 152.80 | 109.60 |
| Styrene (parts) | 100 | 42.70 | 42.70 | 42.70 |
| n-Butyl acrylate (parts) | 0.0 | 57.30 | 57.30 | 57.30 |
| Azo emulsifier B according to Example 5, 10% in water (parts) | 48.0 | 36.0 | 48.0 | 96.0 |
| Polymerisation temperature (°C.) | 60 | 60 | 60 | 60 |
| Polymerisation time (h) | 7 | 7 | 7 | 7 |
| Solids content of latex (%) | 33.5 | 32.4 | 33.1 | 34.2 |
| Precipitate (parts) | 3.7 | 3.2 | 2.2 | 3.3 |
| Particle diameter (nm) according to LCS (latex particles) | 122 | 125 | 115 | 145 |
| Conductivity (mS) | 2.5 | 1.7 | 2.6 | 4.9 |
| Drop count of latex | 26.0 | 35 | 40 | 55 |
| Drop count of water | 25 | 25 | 25 | 25 |
| Foam collapse (sec.) after vigorous shaking for 30 sec. | 60 | 35 | 70 | 250 |

EXAMPLE 7

Polybutadiene latex containing azo emulsifier A 1640 g of deionised water and 1000 g of butadiene are introduced under nitrogen into a 6 liter autoclave. The mixture is then heated to 60° C., after which 360 ml of a 10% solution of azo emulsifier A (according to Example 1) are introduced under pressure into the 6 liter autoclave from a small pressure vessel.

After polymerisation time of 7.5 hours, approximately 3 kg of latex having a solids content of 32.0% by weight are obtained. Following addition of the azo emulsifier, the solids content of samples taken during polymerisation amounts to 1.0% by weight after the first hour,
4.0% by weight after the second hour,
7.0% by weight after the third hour,
14.5% by weight after the fourth hour,
20.5% by weight after the fifth hour,
28.5% by weight after the sixth hour,
30.5% by weight after the seventh hour.

During the polymerisation reaction, the pressure falls from 12.8 bars to 7 bars (at 60° C.).

The coagulate content of the latex amounts to approximately 0.5%, based on polymer. The latex has a particle diameter of 85 nm, is thinly liquid and does not foam, its electrical conductivity amounting to 1.7 mS.

The polymer is largely crosslinked and, accordingly, is only partly soluble (60%).

If the proportion of azo initiator is reduced and, at the same time, a standard emulsifier, such as potassium oleate for example, and a regulator, such as dodecyl mercaptan, are used, the gel content may be reduced.

EXAMPLE 8

PVC-dispersion containing azo emulsifier A 1640 g of deionised water and 1000 g of vinyl chloride are introduced under nitrogen into a 6 liter autoclave after which the mixture is heated to 60° C. After the temperature of 60° C. has been reached, 360 ml of a 10% solution of azo emulsifier A (according to Example 1) are introduced into the 6 liter autoclave from a small pressure vessel. After a polymerisation time of 7 hours, a coarse dispersion having a particle size of approximately 500 to 2000 nm for a solids content of approximately 33% is obtained.

The polymer is soluble in tetrahydrofuran and has a viscosity number [$\eta$] of 0.8 (at 25° C.).

We claim:

1. A surface-active azo compound obtainable by reacting an azo compound corresponding to the formula:

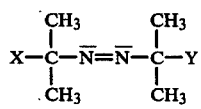

in which X and Y are the same or different and each represents one of the following:

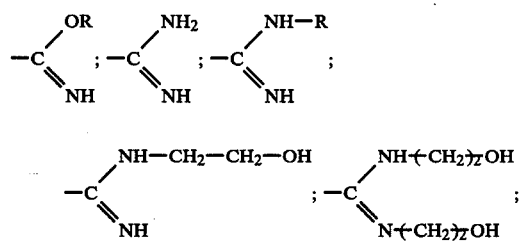

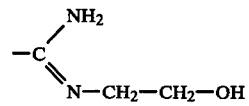

and

R represents $C_1$–$C_4$-alkyl, with at least one $C_{10}$–$C_{18}$-paraffin disulphonic acid dichloride in aqueous medium or in a solvent or a solvent mixture which is inert to the reactants under the process conditions and in which the reactants are at least partly soluble, at a temperature in the range of from 0° to 30° C. and in the presence of a base, the reaction being accompanied by the elimination of hydrogen chloride.

2. A surface-active azo compound, as claimed in claim 1, wherein the paraffin disulphonic acid dihalide is used in a quantity of from 1 to 2 moles per mole of the azo compound.

3. A surface-active azo compound, as claimed in claim 1 or 2, wherein an alkali metal hydroxide or ammonia is used as the base.

* * * * *